United States Patent
McConville et al.

(10) Patent No.: US 8,829,225 B2
(45) Date of Patent: Sep. 9, 2014

(54) PURIFICATION OF 1,1-DISUBSTITUTED ETHYLENE

(71) Applicant: OptMed, Inc., New York, NY (US)

(72) Inventors: Francis McConville, Worcester, MA (US); John Gregory Reid, Groton, MA (US); Murugappa Vedachalam, Raynham, MA (US)

(73) Assignee: OptMed, Inc., New York, NY (US)

( * ) Notice: Subject to any disclaimer, the term of this patent is extended or adjusted under 35 U.S.C. 154(b) by 0 days.

(21) Appl. No.: 13/752,361

(22) Filed: Jan. 28, 2013

(65) Prior Publication Data

US 2013/0310594 A1    Nov. 21, 2013

Related U.S. Application Data

(60) Provisional application No. 61/591,882, filed on Jan. 28, 2012.

(51) Int. Cl.

| | | |
|---|---|---|
| *C07C 253/30* | (2006.01) | |
| *C07C 67/00* | (2006.01) | |
| *B01D 15/00* | (2006.01) | |
| *C07C 67/56* | (2006.01) | |
| *C10G 70/04* | (2006.01) | |
| *C07C 253/34* | (2006.01) | |
| *C07C 231/24* | (2006.01) | |

(52) U.S. Cl.
CPC ............... *C07C 253/30* (2013.01); *C07C 67/00* (2013.01); *B01D 15/00* (2013.01); *C07C 67/56* (2013.01); *C10G 70/046* (2013.01); *C07C 253/34* (2013.01); *C07C 231/24* (2013.01)
USPC ........... 558/443; 560/190; 560/203; 560/185; 558/372; 558/442; 523/400; 524/500; 525/435; 522/170

(58) Field of Classification Search
CPC ...... C07C 67/48; C07C 67/62; C07C 255/06; C07C 255/07; C07C 255/09; C07C 255/10; C07C 255/11; C07C 255/15; C07C 255/16; C07C 255/17; C07C 255/18; C07C 255/19; C07C 255/20; C07C 255/21; C07C 255/22; C07C 255/23; C07C 255/24; C07C 255/26; C07C 255/27; C07C 255/28; C07C 255/29; C07C 255/30; C07C 255/31; C07C 255/32; C07C 69/73; C07C 255/25
USPC .................. 558/372, 443, 442; 560/203, 185; 523/400; 524/500; 522/170; 525/435
See application file for complete search history.

(56) References Cited

U.S. PATENT DOCUMENTS

| | | | |
|---|---|---|---|
| 3,691,239 A | 9/1972 | Hackett et al. | |
| 6,080,905 A | 6/2000 | Kaminsky et al. | |
| 7,569,719 B1 | 8/2009 | McArdle et al. | |
| 2007/0299080 A1* | 12/2007 | Powers et al. | 514/252.1 |
| 2010/0197989 A1 | 8/2010 | Ducreux et al. | |
| 2013/0281580 A1* | 10/2013 | Malofsky et al. | 524/46 |

FOREIGN PATENT DOCUMENTS

| | | |
|---|---|---|
| CN | 1608726 A | 4/2005 |
| GB | 1006939 | 10/1965 |
| JP | 08310979 | 11/1996 |
| JP | 08310979 A * | 11/1996 |

OTHER PUBLICATIONS

Hideo et al. JP 08310979 A, publ. Nov. 1996. Machine Translation (English) obtained Jan. 29, 2014.*

* cited by examiner

*Primary Examiner* — Samantha Shterengarts
*Assistant Examiner* — Amanda L Aguirre
(74) *Attorney, Agent, or Firm* — Edward K. Welch, II; IP&L Solutions (57) ABSTRACT

An improvement in the production of 1,1-disubstituted ethylenes is attained by contacting a 1,1-disubstituted ethylene with alumina and separating the alumina to obtain a 1,1-disubstituted ethylene with a good combination of cost, purity, shelf life and cure rate.

17 Claims, 1 Drawing Sheet

PURIFICATION OF 1,1-DISUBSTITUTED ETHYLENE

RELATED APPLICATION

This patent application claims the benefit of prior U.S. Provisional Patent Application No. 61/591,882 filed Jan. 28, 2012, entitled Improved 1,1-Disubstituted Ethylene Process, McConville et. al., the contents of which are hereby incorporated herein in their entirety.

FIELD OF THE INVENTION

The present invention relates to a process for improving cure speed and/or providing more consistent, i.e., batch-to-batch, cure speed in 1,1-disubstituted ethylene monomers and monomer containing compositions. The present invention also relates to an improved process for the production of 1,1-disubstituted ethylene monomers, including methylidene malonates and cyanoacrylates, especially methylidene malonates, and the use thereof.

BACKGROUND 1,1-disubstituted ethylene monomers and compositions containing the same are well known and, for the most part, widely available. They have utility in a broad array of end-use applications, most notably those which take advantage of their cure or polymerizable properties. Specifically, they find broad utility in coatings, sealants and adhesives, among other applications. Those 1,1-disubstituted ethylenes having one or, preferably, two electron withdrawing substituents at the 1 position have been used to provide adhesives and sealants with rapid cure rates and high bond strengths. Most notable among these are the cyanoacrylates such as ethyl cyanoacrylate, butyl cyanoacrylate and octyl cyanoacrylate. Another class of 1,1-disubstituted ethylenes that have demonstrated a lot of promise, but have limited, if any, commercial success are the methylidene malonates, including diethyl methylidene malonate.

Commercial success of the 1,1-disubstituted ethylenes is reliant upon a number of variables and factors including reasonable cost, high purity, good (especially long) shelf life and rapid cure rate. In an effort to achieve these goals, much work has been done to develop new and/or improved processes and synthetic schemes for their manufacture, purification and isolation.

For example, α-cyano acrylates have been prepared (U.S. Pat. No. 6,245,933) by reacting a cyanoacetate such as ethyl cyanoacetate with formaldehyde or a formaldehyde synthon such as paraformaldehyde in a Knoevenagel condensation followed by transesterification. The product mixture is then cracked and distilled to produce the α-cyano acrylate monomer.

In another preparation (U.S. Pat. No. 7,569,719), ethyl cyanoacetate is reacted with specific iminium salts prepared from paraformaldehyde and primary amines such as t-butyl amine.

In a process disclosed in WO 2010129066, crude diethyl methylidene malonate is prepared from diethyl malonate and paraformaldehyde, subsequently stabilized and distilled, then restabilized and redistilled.

The large amount of work done to explore various synthetic routes and the extremes taken to purify the 1,1-disubstituted ethylenes demonstrate both the importance and the complexity of these materials and their production. While commercial success has been found with the cyanoacrylates, methylidene malonates continue to struggle. Indeed, methylidene malonates have been the subject of decades and decades of efforts to produce them in commercial quantity at a commercially viable price and of suitable cure speed and shelf stability; yet, frustration continues.

Two of the earliest methods for the production of dialkyl methylidene malonates, the simplest of the methylidene malonates, were the iodide method in which methylene iodide was reacted with dialkyl malonates and the formaldehyde method in which formaldehyde was reacted with dialkyl malonates in the presence of a base, in solution in alcohol solvents. The former was unsatisfactory due to very low yield and expensive starting materials. The latter, though periodically giving better yields than the iodide process, gave relatively poor yields and, more critically, was widely inconsistent from batch to batch, even under the same conditions.

Despite its problems, early efforts continued to focus on the formaldehyde method. One of the most widely practiced formaldehyde methods consisted of reacting diethyl malonate with formaldehyde in glacial acetic acid in the presence of a metal acetate catalyst to produce the diethyl methylidene malonate. The latter was subsequently recovered by distillation following removal of the catalyst by filtration and separating off the solvent. These efforts continued to frustrate and various modifications and iterations of this basic process were developed all in an effort to improve the consistency and yields associated therewith.

As an alternative, Bachman et al. (U.S. Pat. No. 2,313,501) taught the reaction of a $C_1$-$C_5$-dialkyl malonate with formaldehyde in the presence of an alkali metal salt of a carboxylic acid, in solution in a substantially anhydrous carboxylic acid solvent, followed by fractional distillation to separate the desired product. Bachman et al. indicate that their process is advantageously carried out in the presence of inhibitors of the polymerization of monomeric vinyl compounds. Suitable inhibitors are said to include the copper salts such as copper chloride and, especially, copper salts of carboxylic acids such as cupric acetate, iron salts such as ferric acetate, and phenols, such as hydroquinone. These are added to the solution mix before the addition of the malonate.

Although Bachman et al. reported yields of up to 72%, the results presented are conversion rates, not yields. Looking at the actual yields of the process, Bachman et al.'s best performance was a yield of 43% with all others being less than 25%. Though Bachman et al. speak of high purity and the ability to recover pure material, they never present any details or data as to what those purities or recoveries were. In any event, Bachman et al. reported that the isolated product, upon standing, polymerized in a day to several weeks time depending upon the purity of the isolated material, which polymer was then heated to a sufficiently high temperature to facilitate the reversion of the polymer to the monomer.

D'Alelio (U.S. Pat. No. 2,330,033), on the other hand, alleged that such processes were erratic and more often produced yields that averaged 10 to 12 percent. D'Alelio espoused an improved process with yields on the order of 30% and higher by reacting a malonic acid ester with formaldehyde in a ratio of one mole of the former to at least one mole of the latter under alkaline conditions and, in most cases, in the presence of a polymerization inhibitor such as copper, copper acetate, hydroquinone, resorcinol, or catechol, to form a methylol derivative. The methylol derivative was then acidified to a pH below 7.0 using a suitable organic or inorganic acid in order to retard further reaction. The acidified mass is then dehydrated to form the corresponding methylidene malonate which is subsequently separated by distillation.

Coover et al. (U.S. Pat. No. 3,221,745 and U.S. Pat. No. 3,523,097) took yet another approach to the formation of the methylidene malonates, electing to begin with a preformed dialkyl alkoxymethylenemalonate. In accordance with their process, the olefinic double bond of the latter compound was subjected to hydrogenation in the presence of a hydrogenation catalyst and the hydrogenated compound was then subject to pyrolysis in the presence of a phosphorous pentoxide inhibitor to strip off the alcohol to produce the methylene malonate. The resultant mass was then subjected to vacuum distillation at low temperature to separate an allegedly high purity methylidene malonate, though with a low yield. According to Coover et al., the use of low temperature distillation is said to prevent the contamination of the monomer with pyrolytic products that commonly result from high temperature distillation. These high purity monomers are said to be especially important for surgical applications.

Eventually, such efforts led to multi-step processes in which certain unsaturated molecules served as a platform for the formation of intermediate adducts from which the methylidene malonates were subsequently stripped and recovered. For example, Hawkins et al. (U.S. Pat. No. 4,049,698) found that certain malonic diesters could be reacted with formaldehyde and a linear, conjugated diene in the presence of a primary, secondary or tertiary amine at about reflux temperature to form an intermediate adduct that could then be readily pyrolyzed at temperatures in excess of 600° C. to split off the desired methylidene malonate. Similarly, Ponticello (U.S. Pat. No. 4,056,543) and Ponticello et al. (U.S. Pat. No. 4,160,864) developed processes by which asymmetrical methylene malonates, especially methyl allyl methylene malonate, were prepared from previously formed norbornene adducts, the latter having been prepared by the Diels-Alder reaction of an alkyl acrylate with cyclopentadiene at room temperature or with heating or use of a Lewis catalyst. The so formed monoester norbornene adducts were then reacted with an electrophile material in the presence of an alkyl-substituted lithium amide complex to form the diester adduct and subsequently pyrolyzed at a temperature of 400° C. to 800° C. at a pressure of 1 mm to 760 mm Hg in an inert atmosphere to strip off the desired methylene malonates. These efforts, despite their gains in yield and/or purity, still failed to achieve commercial success.

Citing numerous disadvantages of the foregoing processes, which disadvantages were said to make them difficult, if not impossible, to adapt to industrial scale, Bru-Magniez et al. (U.S. Pat. No. 4,932,584 and U.S. Pat. No. 5,142,098) developed a process whereby anthracene adducts were prepared by reacting mono- or di-malonic acid ester with formaldehyde in the presence of anthracene, most preferably in a non-aqueous solvent medium in the presence of select catalysts.

According to Bru-Magniez et al., the anthracene adducts were said to be readily produced in high yields with the desired methylidene malonates obtained by stripping them from the anthracene adduct by any of the known methods including heat treatment, thermolysis, pyrolysis or hydrolysis; preferably heat treatment in the presence of maleic anhydride. The resultant crude products were then subjected to multiple distillations, preferably lower temperature distillations under vacuum, to recover the purified methylidene malonate. Despite the claim to high yields, their crude yields were generally in the range of 21-71%, more importantly, nothing is said with respect to the purity of the material obtained.

Based on conversations with the successors to the Bru-Magniez technology, efforts to commercially produce the material have met with great difficulty owing to the high instability of the overall production process and final products. Indeed, they reported a high failure rate: of the limited batches that actually survived through crude distillation, the resultant products had to be stored in a freezer even after stabilizing with upwards of 50,000 ppm $SO_2$ due to their high instability and spontaneous polymerization.

Malofsky et al. (WO 2010/129068) solved some of the problems associated with process instability of the Retro-Diels-Alder adduct process by using polymerization inhibitors concurrent with or prior to stripping of the adduct. Inhibitors such as trifluoroacetic acid and hydroquinone were used. In some examples, trifluoroacetic acid was also added to the distillate. Only limited curing studies were done, but the resultant malonates were able to be polymerized with tetrabutylammonium fluoride. Malofsky teaches a variety of purification processes including double distillation and extracting the product with an alkane such as n-heptane. Although this is an improvement over the art, these various purification processes can be costly and can reduce yield.

The problems of producing 1,1-disubstituted ethylene with a good combination of cost, purity, shelf life and rapid cure rate is not specific to methylidene malonates or to a particular method of production. Imohel et al. (U.S. Pat. No. 3,728,373) teaches the use of hydroquinone and other polymerization inhibitors with polycyanoacrylates and decomposes these and distills cyanoacrylates from the polymer/stabilizer mixture. More recently, Malofsky et al. (U.S. Pat. No. 6,512,023) theorized that the stability of 1,1-disubstituted ethylene monomer and polymers could be improved by the use of specific combinations of certain vapor phase and certain liquid phase anionic polymerization inhibitors. These monomers, typically cyanoacrylates, exhibited improved stability. McArdle (U.S. Pat. No. 7,973,119) prepares electron deficient 1,1-disubstituted ethylene compounds such as cyanoacrylates and methylidene malonates by an entirely different process using protonated imines. McArdle teaches the use of free radical and acidic stabilizers.

The large amount of work as well as the numbers of scientists who have endeavored to deal with these problems is a testament to the perceived importance of 1,1-disubstituted ethylene monomers, including methylidene malonates and cyanoacrylates, and the complexity involved in the production thereof, most especially the methylidene malonates, and the use thereof. Reaction viability (i.e., the ability to isolate product before cure), low yields, low purity, poor shelf life or the need for extreme storage conditions, and cure rate are erratic and have and continue to frustrate those efforts to overcome the same. For sure, improvements in stabilization techniques and technology, both of the final product and in the isolation thereof, have dramatically improved reaction viability, yields, purity and shelf life; however, cure speed remains erratic and unpredictable. While, from a purely technical perspective cure speed may not be critical; from a commercial perspective it is highly critical. Commercial utility is severely limited, if not wanting, and the prior improvements are largely meaningless, if one is unable to show or establish consistent and/or predictable cure speeds. Curable compositions need defined cure speed or cure speed parameters for utility in commercial, medical, and industrial applications.

However, a discontinuity exists in that the two desired properties, namely excellent shelf life and a rapid or predictable cure rate are often at cross purposes and one must be compromised at the expense of the other. Excellent shelf life implies good stability and a resistance to polymerization whereas a rapid cure rate implies a highly active and, hence, unstable, product whose tendency is to rapidly polymerize. Additional complexity in the production of these monomers lies in the fact that many purification techniques involve high temperature, e.g., distillations, and/or conditions which accelerate polymerization and/or increase instability of the material being worked upon. As a result, polymerization and/or degradation of the materials being worked on can occur. Indeed, the production of cyanoacrylate takes advantage of this effect, allowing the monomer to polymerize and then cracking the monomer in the presence of certain stabilizers, to effectively regenerate the monomer. However, this process is not amenable to or suitable for the production of most 1,1-disubstituted ethylenic monomers, especially the methylidene malonates.

Thus, there remains a need for a new and/or improved process for the production of 1,1-disubstituted ethylenic monomers, especially methylidene malonates, which provides consistent production viability with high yields and purity and good shelf life as well as rapid and consistent or predictable cure speeds.

SUMMARY OF THE INVENTION

According to the present teachings there is provided a method of improving cure performance of 1,1-disubstituted ethylene monomer, dimer, trimer, oligomers and low molecular weight polymers and combinations thereof. In particular, there is provided a method of providing 1,1-disubstituted ethylene monomer, dimer, trimer, oligomers and low molecular weight polymers and combinations thereof having faster and/or consistent and more predictable (from a batch-to-batch perspective) cure speeds. Specifically, it has now been found that by treating 1,1-disubstituted ethylene monomer, dimer, trimer, oligomers and low molecular weight polymers and combinations thereof with a slightly acidic to moderately basic alumina, one is able to increase cure speed as well as control and/or provide more consistency and/or predictability to the cure speed of the materials treated.

According to a second aspect of the present teachings there is provided an improved process for the production and isolation of 1,1-disubstituted ethylene monomer, dimer, trimer, oligomers and low molecular weight polymers and combinations thereof wherein the improvement comprises treating the 1,1-disubstituted ethylene monomer, dimer, trimer, oligomers and low molecular weight polymers and combinations thereof with a slightly acidic to moderately basic alumina. Treatment may be prior to, in the course of, or subsequent to those steps employed to separate/isolate and/or purify the 1,1-disubstituted ethylene monomer, dimer, trimer, oligomers and low molecular weight polymers and combinations thereof. Preferably, the treatment is performed following the last, if any, high temperature distillation or evaporation or like process.

According to a third aspect of the present teachings there is provided compositions comprising 1,1-disubstituted ethylene monomer, dimer, trimer, oligomers and low molecular weight polymers and combinations thereof resulting from the aforementioned methods which compositions have improved and more consistent cure speeds as compared to the same compositions which have not been subjected to the alumina treatment. In this regard, the present teachings also relate to a method of custom tailoring cure speed by adjusting the treatment process and/or blending quantities of the treated materials.

Although the present teachings are applicable to 1,1-disubstituted ethylenes generally, it is especially applicable to those monomers whose stability and/or polymerization is adversely affected by the presence of acids or acid species. In particular, the present teachings are especially applicable to cyanoacrylates and methylidene malonates, most especially methylidene malonates, whose polymerization is slowed, if not fully inhibited, by the presence of acids and acid species.

As noted, the present invention lies in the use of alumina as a treatment for the 1,1-disubstituted ethylenes. Alumina suitable for use in the practice of the present teachings are those having a mildly acid to moderately basic pH. Preferably, the alumina has a pH, as measured in neutral water, of from about pH 5.5 to pH 8.5, more preferably from about pH 6 to pH 8.

The alumina treatment may be conducted in any suitable manner for contacting the 1,1-disubstituted ethylene monomer, dimer, trimer, oligomers and low molecular weight polymers and/or combinations thereof with alumina. Typically, the processing is performed in a batch or batch modified continuous manner: the latter involving the recirculation of a given quantity of the composition to be treated through a column of alumina until the desired contact time is attained. Of course, continuous processing is also suitable provided that the contact time between the alumina and the material being treated is sufficient to provide the desired effect on cure speed.

Typically, the alumina treatment is conducted at from about 0° C. to about 150° C., preferably from about 20° C. to 70° C., for from about 5 minutes to about 20 hours, preferably from about 10 minutes to 5 hours. The quantity of alumina employed depends upon many factors, including the method employed. Generally speaking, especially in batch processing, the amount of alumina is from about 0.5 to about 20 weight percent, preferably from about 2 to about 10 weight percent, based on the weight of the monomer. Higher concentrations may be employed, but such higher concentrations make it difficult to stir the materials and result in loss of monomer due to surface wetting of the alumina with the monomer.

DETAILED DESCRIPTION

The present teachings provide, in one aspect, a new method for the treatment of 1,1-disubstituted ethylenes, especially monomers, though it is equally applicable to dimers, trimers, oligomers and low molecular weight polymers thereof, and combinations of any two or more of the foregoing whereby cure speed and/or cure speed control or predictability is improved. Specifically, there is provided a method whereby said 1,1-disubstituted ethylenes are treated with certain alumina materials, specifically an alumina having a slightly acidic to moderately basic pH, so as to improve cure speed and/or cure speed predictability. In a second aspect, the present teachings provide for an improved method for the production and/or isolation or purification of 1,1-disubstituted ethylenes wherein the method further comprises the step of treating the crude product or a purified or partially purified reaction product with certain alumina materials, specifically an alumina having a slightly acidic to moderately basic pH. Finally, the present teachings provide and claim the treated 1,1-disubstituted ethylenes processed in accordance with the present teachings as well as compositions comprising the same.

In its most broad concept, the present teachings apply to 1,1-disubstituted ethylenes having at least one electron withdrawing substituent at the one position with the preferred electron withdrawing groups being selected from nitriles (including cyano), nitro, carboxylic acids, carboxylic acid esters, sulphonic acids and esters, amides, ketones and formyl; especially cyano and carboxylic acid esters preferably cyano and carboxylic acid esters. Although, as noted above and herein, the present teachings are applicable to 1,1-disubstituted ethylenic monomers, dimers, trimers, oligomers and low molecular weight polymers as well as combinations of any two or more of the foregoing, for the sake of simplicity and brevity, the following discussion will be made with reference to the monomer, though it is to be appreciated that it is not limited thereto. Indeed, experience has shown that most reaction processes for 1,1-disubstituted ethylenes, especially the methylidene malonates produce combinations of monomer, dimer, trimer, oligomers and/or low molecular weight polymers.

The present process is applicable to the production of 1,1-disubstituted ethylene monomers generally, especially, but not limited to those having the general formula I:

wherein R is H or $C_1$ to $C_6$ hydrocarbyl such as methyl, ethyl, ethenyl, propyl, propenyl, isopropyl, isopropenyl, butyl, or phenyl and X and Y are independently selected from $C_1$ to $C_{12}$, preferably $C_1$ to $C_{10}$, most preferably $C_2$ to $C_8$, hydrocarbyl or heterohydrocarbyl groups provided that at least one of X and Y is a strong electron withdrawing group. Exemplary strong electron withdrawing groups include, but are not limited to, cyano, carboxylic acid, carboxylic acid esters, amides, ketones or formyl and Y is cyano, carboxylic acid, carboxylic acid esters, amides, ketones, sulfinates, sulfonates, or formyl. Monomers within the scope of Formula I include α-cyanoacrylates, vinylidene cyanides, alkyl homologues of vinylidene cyanide, methylidene malonates, dialkyl methylene malonates, acylacrylonitriles, vinyl sulfinates, and vinyl sulfonates.

Exemplary preferred 1,1-disubstituted ethylene monomers of formula I include, but are not limited to:

Exemplary preferred 1,1-disubstituted ethylene monomers are those of the formula II:

where $R^2$ is H or —CH═CH$_2$, most preferably H; and X and Y are each independently —CN or —COOR$^3$ wherein $R^3$ is:
a hydrocarbyl or substituted hydrocarbyl group;
a group having the formula —R$^4$—O—R$^5$—O—R$^6$, wherein $R^4$ is a 1,2-alkylene group having 2-4 carbon atoms, $R^5$ is an alkylene group having 2-4 carbon atoms, and $R^6$ is an alkyl group having 1-6 carbon atoms; or
a group having the formula wherein $R^7$ is —(CH$_2$)$_n$—; —CH(CH$_3$)—; or —C(CH$_3$)$_2$— wherein n is 1 to 10, preferably 1-5, and $R^8$ is H or an organic moiety, preferably a hydrocarbyl or substituted hydrocarbyl. Suitable hydrocarbyl and substituted hydrocarbyl groups include, but are not limited to, $C_1$-$C_{16}$, preferably $C_1$-$C_8$, straight chain or branched chain alkyl groups; $C_1$-$C_{16}$, preferably $C_1$-$C_8$, straight chain or branched chain alkyl groups substituted with an acyloxy group, a haloalkyl group, an alkoxy group, a halogen atom, a cyano group, or a haloalkyl group; $C_2$-$C_{16}$, preferably $C_2$-$C_8$, straight chain or branched chain alkenyl groups; $C_2$-$C_{12}$, preferably $C_2$-$C_8$, straight chain or branched chain alkynyl groups; and $C_3$-$C_{16}$, preferably $C_3$-$C_8$, cycloalkyl groups; as well as aryl and substituted aryl groups such as phenyl and substituted phenyl and aralkyl groups such as benzyl, methylbenzyl, and phenylethyl. Substituted hydrocarbyl groups include halogen substituted hydrocarbons such as chloro-, fluoro- and bromo-substituted hydrocarbons and oxy-substituted hydrocarbons such as alkoxy substituted hydrocarbons.

Exemplary preferred 1,1-disubstituted ethylene monomers include, but are not limited to:

H$_2$C═C(CN)CO$_2$(CH$_2$)$_3$CH$_3$, H$_2$C═C(CN)CO$_2$(CH$_2$)$_5$CH$_3$ and H$_2$C═C(CN)CO$_2$(CH$_2$)$_7$CH$_3$.

The 1,1-disubstituted ethylene monomers formed by the improved process of the present invention may be employed in a number of organic syntheses and polymer chemistry applications. In particular, they are especially useful in the preparation of various adhesive and sealant applications including industrial, commercial and consumer adhesive and sealant applications as well as in medical and medical device applications, including tissue bonding, especially human and animal skin bonding. In light of the benefit of the present invention, it is believed that these compositions are now commercially viable and provide a desirable balance of cost, purity, shelf life and cure rate. Specifically, the processes of the present teachings provide 1,1-disubstituted ethylene monomers, especially methylidene malonate monomers, having improved cure control and repeatability as compared to the same monomers which have not been processed as presently claimed.

The 1,1-disubstituted ethylene monomer is contacted with alumina. Alumina, also called aluminum oxide ($Al_2O_3$), is widely available. Most aluminum metal is prepared from alumina. Alumina is available in a variety of grades, particle sizes, pore diameters, surface areas, and pHs. Preferably, the alumina is porous and has a large surface area. More preferably, the average surface area is from 100 $m^2$/g to 250 $m^2$/g, or larger.

Preferably the alumina is activated alumina. The term "activation" refers to the heat treatment normally used to create the high surface area and to drive off water. A scale, Brockmann I-V, measures alumina activity by the amount of water present on the alumina. Commercially available activated alumina is typically Brockmann I and has a relatively low percent moisture, about 1 or 2% by Karl-Fischer titration. Brockmann II has about 4-4.5% water; Brockmann III about 7-7.5% water; Brockmann IV about 11-11.5% water; and Brockmann V about 16-16.5% water. Water can be added to Brockmann I to partially deactivate it to a higher Brockmann number. Similarly, alumina which has absorbed/adsorbed moisture can be heat treated, e.g., heating to 50° C. to drive moisture off, to increase the activity and lower the Brockmann number. Preferably, the alumina has an activity corresponding to I or II on the Brockmann scale, more preferably the alumina has an activity corresponding to I on the Brockmann scale.

Alumina is available as basic alumina, neutral alumina and acidic alumina. When alumina is slurried in water, the pH can be measured. Basic alumina has a pH greater than 8, generally from about 9-10; neutral alumina has a pH of about 6-8; and acidic alumina has a pH of less than 6, generally from about 4-5. For use in the practice of the present process, the alumina preferably has a pH from mildly acidic to moderately basic, generally from about 5.0 to about 8.5, preferably from about 5.5 to about 8.5, more preferably from about 6.0 to about 8.0, most preferably from about 6.5 to about 7.5: pH being determined on the basis of a slurry of the alumina in neutral or near neutral deionized water.

The 1,1-disubstituted ethylene can be contacted with the alumina by any of a variety of methods. One preferred method is a batch method wherein a slurry or intimate mixture is formed of the alumina and the 1,1-disubstituted ethylene monomer, which may be in neat form or in solution, and the slurry or mixture is allowed to stand, generally with stirring, for the desired period of time. Another preferred method, which may be performed in a continuous or batch-type manner, is to pass the 1,1-disubstituted ethylene monomer or a solution thereof through a column of alumina. The latter can be modified to allow for a true continuous processing by using a column of an appropriate or suitable length or one which is adapted to allow for the recirculation of the 1,1-disubstituted ethylene though the column to allow for the proper overall residence or contact time with the alumina. Regardless of the method chosen, it is preferred that the 1,1-disubstituted ethylene monomer be contacted with the alumina at a temperature from 0° C. to 150° C., preferably from about 20° C. to about 70° C. Lower temperatures, while suitable for the purpose of the method, are unnecessary and add to the overall cost, both in terms of cooling costs and the time required to effect the necessary treatment. Higher temperatures likewise are unnecessary and, depending upon how high one raises the temperature, can cause degradation or polymerization of the 1,1-disubstituted ethylene monomer.

The duration of the treatment depends upon a number of variables pertaining to the materials used and to be treated, the weight ratio of alumina to 1,1-disubstituted ethylene monomer, the method and conditions of treatment as well as the desired properties, especially cure performance, of the treated 1,1-disubstituted ethylene monomer. For example, the alumina selected, the temperature at which the treatment is performed, the purity of the 1,1-disubstituted ethylene monomer, and the desired cure rate can all influence the preferred contact time between the alumina and the 1,1-disubstituted ethylene monomer. Generally speaking, the longer the contact time, the faster the cure rate of the treated monomer. However, as the contact time increases, longer and longer, the effect on cure speed appears to level off such that further lengthening of the contact time does not or does not appear to provide any significant improvement or increase in cure speed. In any event, proper contact times for the systems, methods and desired cure speed can be found by simple trial and error. Generally speaking, though, it has been found that good cure performance can be attained by employing typical contact times of from about 5 minutes to about 20 hours, preferably from about 10 minutes to about 5 hours, more preferably from about 10 minutes to 150 minutes. Of course, consideration must also be given to the desired cure speed. Immediate or extremely fast cure, seconds to a minute or less, may be suitable and desirable for some applications; whereas longer cure times of a minute to five minutes or more may be more appropriate for another application. Thus, one may elect to stop the treatment before the maximum possible cure speed is attained.

The weight ratio of alumina to 1,1-disubstituted ethylene monomer can be varied widely and, as with the contact time, is dependent upon a number of variables including the contact time desired, the contact temperature, the purity of the 1,1-disubstituted ethylene monomer (especially the cure speed of the unmodified monomer) and the desired cure rate. Generally speaking, for batch processing, the amount of alumina to be added to the 1,1-disubstituted ethylene monomer is from about 0.5 to about 20 weight percent, preferably from about 1 to about 15 weight percent, more preferably from about 2 to about 10 weight percent, most preferably from about 4 to about 7 weight percent, based on the weight of the monomer. Higher levels, e.g., up to 25 wt. %, 30 wt. %, or more, can be used and are effective, especially for highly inactive monomers; however, particularly where the monomer is being treated in its neat form, it is preferable to use lower amounts of alumina, generally as low as possible for the desired effect on cure speed as monomer inherently binds to the surface of the alumina during the treatment process and is lost during recovery: hence reducing yields. However, care must also be taken to balancing process economics so as not to employ too low an amount of alumina whereby treatment time is unnecessarily long or extended leading to increased production costs and exposing the monomer to higher temperatures for longer times which may concurrently affect yields and purity. Additionally, it is to be appreciated that higher and higher amounts of alumina also thicken the slurry making stirring and/or separation difficult. Again, the foregoing are general ranges and may well vary depending upon a number of factors, especially the alumina employed and the purity and/or cure speed of the 1,1-disubstituted ethylene monomer before treatment.

Where the monomer is to be passed through the alumina, rather than mixing the alumina into the monomer, the amount of alumina is much higher in relation to a given quantity of monomer to be treated. Here, one typically fills a column with the alumina and then passes the monomer through that column one or more times. In this case, one looks to the amount of alumina to the total volume of monomer treated or passed through. Through simple trial and error, one can gauge how much monomer one can pass through a particular column for a particular effect. Specifically, a loss in cure speed from the initial volume of monomer treated and a later volume of monomer treated in the same column will be indicative of a loss in efficacy of the alumina and a need to replace it. It is also possible to estimate the life of the alumina by correlating the total amount of alumina in the column to the quantity of monomer treated with the ranges set forth above for the batch treatments. Generally, one would expect the same overall quantity of alumina to be capable of treating the same overall quantity of monomer whether the treatment is by the batch method or a continuous/columnar method.

To help in gauging the proper level of alumina to use, one can also look to the activity of the monomer to be treated. Generally speaking, if the monomer is essentially inactive, i.e., has a DMDEE induction time (as defined below) of greater than 40 minutes, then the amount of alumina to be used will tend to be higher, generally 7% by weight or more, preferably at least 8% by weight. If the monomer is weakly active, e.g., an induction time of less than 40 minutes but still more than 25 minutes, then the amount of alumina should generally be at least 5%, preferably at least 6% by weight, up to about 8% or more. A moderately active monomer, e.g., one having an induction time of between 15 and 25 minutes, can be sufficiently treated with from about 3% to about 6%, preferably from about 4% to about 5% by weight alumina. For more active monomer, especially those where activity is not in question but consistency from batch to batch is, treatment with lesser amounts of alumina are suitable, typically 4% or less by weight. Again, these amounts are general amounts and higher or lower amounts may be suitable for a given monomer and alumina and/or depending upon the desired economics versus cure speed of the final 1,1-disubstituted ethylene.

Similarly, in gauging the proper duration for the contact between the alumina and the monomer, one can also look to the activity of the monomer to be treated as well as the efficacy of the alumina in altering cure speed. Treatment of a monomer that is weakly active with an alumina that provides moderate cure speed impact may take many hours, five or more hours, to reach a desirable cure speed. Conversely, treatment of a monomer that is moderately active with an alumina that is highly effective in impacting cure speed may require but a few minutes treatment. Of course, the quantity of alumina also affects the needed duration of the treatment, with the use of larger quantities of alumina generally reducing the duration of the treatment. Once again, simple trial and error, based on the teachings herein, will allow one to determine the best or optimal times, weight ratios and selection of alumina for a given or desired result.

Another benefit of the present teachings is that one can custom design cure speeds for a given monomer material. Specifically, by tracking the variables of weight ratios, alumina and alumina characteristics, treatment duration, and cure speed of the monomer to be treated and following treatment, one can plot and calculate the needed conditions to effect a given or desired cure speed for a given monomer. Thus, one is able to adjust the variables to produce a monomer with a given or desired cure speed. Furthermore, particularly with those materials treated in the continuous or modified continuous treatment process described above, one can blend the treated products from different treatment runs through the alumina to, again, customer design, the final cure speed of the monomer product. In this regard, as noted above, continuously running untreated monomer through an alumina column will gradually result in a loss or degradation in the ability of the alumina to affect cure speed. Thus, by mixing monomer which passes through the column while it is fresh with monomer that passes through the same column that had been used repeatedly, one is able to customize the overall cure speed of the combined monomer material.

Following treatment, the treated alumina is separated from the 1,1-disubstituted ethylene monomer by any of the known methods for separating a liquid from a solid. Of course where the process is performed with a column of alumina, separation is merely a matter of collecting the monomer as it passes through the column, or in the case of a circulating column, of collecting or drawing off the treated monomer following the proper residence time. In the case of non-columnar treatments, e.g., batch treatments, the treated monomer may be recovered by simple filtration, centrifugation, thin film evaporation, pot distillation, etc.: however in the case of distillation and those processes involving higher temperatures, care must be taken to avoid polymerization and/or the formation of impurities. Furthermore, high temperature processes are preferably avoided as indications are that such high temperature distillation following alumina treatment may negate, in whole or in part, the improvement in cure speed arising from the alumina treatment.

Most preferably, particularly where there is concern for the potential of premature polymerization, the treatment process is performed on stabilized monomer. Similarly, it is preferred to up-stabilize the treated monomer once recovered from the alumina mix. Suitable stabilizers and stabilizer systems are known, though the preferred stabilizers, especially for the methylidene malonates, are the reaction phase stabilizer systems and/or separation phase stabilizer systems of Malofsky et. al. as disclosed in US Published Patent Application Nos. US2010/0286438A1 and US2010/0286433A1, the contents of which are hereby incorporated herein by reference in their entirety.

The process of the present specification may be performed on 1,1-disubstituted ethylene monomers, (which again, may be monomers, dimers, trimers, oligomers, low molecular weight polymers, or mixtures thereof). Where the materials comprise polymers, the molecular weight is preferably such that the material is still in liquid or flowable form, either in neat form or in solution; most preferably it is a liquid in neat form. The 1,1-disubstituted ethylene monomer subjected to the process of the present specification may be formed by any of the methods known in the art, including, especially, those described in the background section above.

In addition, it is to be appreciated that the present process may be integrated into known methods for the production and isolation/purification of 1,1-disubstituted ethylene monomers. Specifically, rather than wait to perform the present treatment process on the isolated and/or purified 1,1-disubstituted ethylene monomer, one can perform the present treatment prior to, during, or as an intermediate step in the course of the isolation and purification process of the 1,1-disubstituted ethylene monomer. For example, in the case of those processes which result in a polymer or gel material which must be cracked to generate the monomer (e.g., the preparation of cyanoacrylates and certain methylidene malonates), the present process may be conducted immediately following the cracking, prior to any other isolation and/or purification step, if any. The present process is especially applicable to those processes where the monomer or a crude monomer is produced in liquid form (does not require cracking) and is subsequently subjected to any number of separation and isolation or purification steps. In these instances, the present process is preferably employed once the crude liquid monomer is isolated. However, it is contemplated that the present process may be performed on the crude reaction product for the production of the 1,1-disubstituted ethylene monomer prior to separation of the crude liquid monomer from the solids. Here, the solids would be removed concurrent with the removal of the alumina. Most preferably, the alumina treatment process is conducted on the isolated monomer, particularly where isolation is by means of distillation or other higher temperature processes. Similarly, if subsequent purification steps involve distillation or high temperatures, again it is preferred that the alumina treatment be conducted following such steps.

The present process is especially suitable/suited for integration into the processes for the production of methylidene malonates, either those employing a direct method, i.e. direct synthesis of the monomer from reactants, or by the adduct process, typically a reverse Diels-Alder adduct process. Examples of such processes are disclosed in the background section above and the art noted therein, all of which are hereby incorporated herein by reference in their entirety. Typically these processes employ at least one and most often two or more distillations of the reaction product in order to improve the purity of the product thereof. These distillations are oftentimes performed under reduced pressure so as to enable lower pot temperatures which decreases degradation and/or polymerization in the pot. Thus, the alumina treatment may be done prior to or between successive distillation steps; though it is most preferably done following the final distillation.

As noted above, in a preferred embodiment of the present process stabilizers are added to the slurry of alumina and monomer, to the 1,1-disubstituted ethylene monomer following removal of the alumina, or both. Where distillation or another higher temperature process is employed as the method for separation of the treated 1,1-disubstituted ethylene monomer from the alumina, it is preferable to add a stabilizer to the slurry prior to or during, preferably prior to, initiation of the purification/recovery process in order to inhibit polymerization. A stabilizer is also preferably added to the collected 1,1-disubstituted ethylene monomer, regardless of whether the monomer is promptly incorporated into a product or intermediate formulation (e.g., an adhesive product), stored for subsequent use, or subjected to one or more additional distillation steps. Here the stabilizer may be added to the collected material after collection or, preferably, a portion thereof is added to the collection vessel prior to initiation of the distillation and additional stabilizer is added, as necessary, to properly stabilize the quantity of 1,1-disubstituted ethylene monomer collected. Preferably, the stabilizer is a stabilizer system comprising at least one liquid phase anionic polymerization inhibitor alone or in combination with a free radical polymerization inhibitor, most preferably a combination thereof. Gas phase and dual liquid-gas phase anionic polymerization inhibitors may also be used; however, these are typically used in combination with a liquid-only phase anionic polymerization inhibitor as well. Exemplary stabilizer systems are disclosed in Malofsky et. al. US2010/0286438A1, US2010/0286433A1, and U.S. Pat. No. 6,512,023, all of which are hereby incorporated herein by reference in their entirety.

Suitable anionic polymerization inhibitors include strong acids and combinations thereof, secondary anionic polymerization inhibitors (i.e., anionic polymerization inhibitors other than strong acids, preferable weak or moderate acids) and combinations thereof, or combinations of both strong acids and secondary anionic polymerization inhibitors. As used herein, a strong acid is an acid that has an aqueous pKa of about 2.0 or less and a very strong acid is one having an aqueous pKa of 1.0 or less. Strong acids include, but are not limited to strong mineral acids and strong organic acids including maleic acid, difluoroacetic acid, dichloroacetic acid, and picric acid. The very strong acids include, but are not limited to the very strong mineral and/or oxygenated acids as well as the sulfonic acids. By way of example, but not limitation, exemplary very strong acids include sulfuric acid, nitric acid, perchloric acid, trifluoroacetic acid, trichloroacetic acid, hydrochloric acid, hydrobromic acid, benzenesulfonic acid, methanesulfonic acid, trifluoromethanesulfonic acid, fluorosulfonic acid, chlorosulfonic acid, para-toluene sulfonic acid, and the like. Preferably the strong acid anionic polymerization inhibitor is selected from trifluoroacetic acid, sulfuric acid, perchloric acid, maleic acid or chlorosulfonic acid, most preferably sulfuric acid and/or trifluoroacetic acid. The latter has the added benefit of serving as both a liquid and vapor phase inhibitor because a sufficient amount distills over with the monomer: thereby stabilizing the vapor phase as well.

Secondary anionic polymerization inhibitors are typically weak or moderate acids and, while they may be used instead of a strong acid, are preferably used in combination with a strong acid. Suitable secondary anionic polymerization inhibitors include vapor phase anionic polymerization inhibitors such as sulfur dioxide, boron trifluoride, or hydrogen fluoride, or combinations of any two or all three as well as liquid phase anionic polymerization inhibitors that do not meet the aforementioned requirements of a suitable strong acid. Such secondary liquid phase anionic inhibitors include those acids having an aqueous pKa of more than 2 and/or having low conductivity in the non-aqueous medium. Exemplary secondary liquid phase anionic inhibitors include, but are not limited to phosphoric acid; organic acids such as acetic acid, benzoic acid, chloroacetic acid, cyanoacetic acid and mixtures thereof, especially acetic acid, benzoic acid or mixtures thereof.

Because the present invention is not limited to aqueous systems, it is to be noted that not all acids dissociate to the same degree in different medium. Hence, it is to be understood that, especially in the context of non-aqueous based systems and media, the strong acids and very strong acids must exhibit sufficient dissociation to manifest a sufficient degree of the acid effect on polymerization inhibition. The degree of dissociation may be determined empirically by measuring the conductivity of the medium to which the acid is added: a higher conductivity being evidence of a greater degree of dissociation. Additionally, with certain exceptions, it is preferred that the chosen polymerization inhibitors, whether for aqueous or non-aqueous systems, are such that they will not readily distill over during the distillation process of the crude material or the subsequent distillations. Rather, it is generally preferred that no or negligible amounts of the polymerization inhibitors distill over. The exception, however, are those polymerization inhibitors that distill over slowly or at an equivalent or near equivalent rate (e.g., stabilizers of the same or similar molecular weight as the monomer) so as to remain in sufficient quantities in the distillation vessel to prevent premature polymerization prior to completion or substantial completion of the distillation process and which also serve as a polymerization inhibitor of the vapor phase as it traverses to the collection flask.

Generally speaking, the amount of anionic polymerization inhibitor to be added to the system should be from about 1 to about 10,000 ppm, preferably from about 5 to about 6000 ppm, most preferably from about 30 to about 2000 ppm, based on the amount of 1,1-disubstituted ethylene monomer. Generally, the amount of anionic polymerization inhibitor to use can be determined by simple experimentation. Because these stabilizers will affect the cure speed of the 1,1-disubstituted ethylene monomers, care must be taken to ensure that one does not add excessive amount of stabilizer; otherwise, one may cause the cure speed to be so slow as to render the composition ineffective for its intended use or may prevent cure altogether. Proper levels can be attained by simple trial and error.

Suitable free radical inhibitors include, but are not limited to, the quinones, hindered phenols, and combinations thereof. Preferred free radical inhibitors include the hydroquinones, hydroquinone monomethyl ether, catechol, pyrogallol, benzoquinones, 2-hydroxy benzoquinones, p-methoxy phenol, t-butyl catechol, butylated hydroxy anisole (BHA), butylated hydroxy toluene (BHT), t-butyl hydroquinones, 2,2'-methylene-bis(6-tert-butyl-4-methylphenol), and mixtures thereof. Generally speaking the amount of free radical inhibitor to be added to the system should be from about 100 to about 20,000 ppm, preferably from about 300 to about 10,000 ppm, most preferably from about 2000 to about 5000 ppm based on the amount of 1,1-disubstituted ethylene monomer. Generally, the amount of free radical polymerization inhibitor to use can be determined by simple experimentation. Though perhaps less critical than with the anionic polymerization inhibitor, care should be taken to ensure that one does not add too much free radical polymerization inhibitor out of concern that it will prevent polymerization when it is desired.

In one of the preferred embodiments of the present process, a stabilizer system comprising at least one anionic polymerization inhibitor and a free radical polymerization inhibitor is added to the crude liquid 1,1-disubstituted ethylene monomer prior to further purification thereof, Such monomer may arise from any of the known processes for the production thereof including the direct or reverse Diels-Alder adduct process or the iminium based process. The stabilized crude liquid monomer product is distilled under reduced pressure one or more times, preferably with each distillate being similarly stabilized. The distillate is then contacted with alumina, with or without a stabilizer system, for the desired period of time and subsequently separated from the alumina. The same or a different stabilizer is then added to provide stabilized a 1,1-disubstituted ethylene monomer manifesting good purity, shelf life and cure speed, all at a reasonable cost. Where a stabilizer has been added to the alumina/1,1-disubstituted ethylene monomer slurry, one will typically up-stabilize the separated monomer as necessary due to the tendency of the alumina to adsorb acid stabilizers.

The 1,1-disubstituted ethylene monomers produced in accordance with the present specification may be used in a broad array of applications, as known to those skilled in the art. They are especially suited as components of adhesive and sealing compositions, including as skin bonding adhesives for medical, surgical, dental and veterinary use. As noted above, and as evident from the following examples, the 1,1-disubstituted ethylene monomers have a combination of good shelf stability, high purity and controlled and consistent cure speed: properties which are not always attainable by those 1,1-disubstituted ethylene monomers which have not had the benefit of the alumina treatment, at a reasonable cost. While shelf stability and purity are important, it is especially to be noted that proper cure speed (for the application) and consistent cure speed are equally, if not more, important. In this regard, consistent cure speeds or cure times are critical for industrial in-line bonding applications, medical applications, and the like. Generally speaking, cure speed of less than 10 minutes are most typical, with certain applications, like consumer and industrial bonding, having cure speeds of a matter of seconds to a minute or two. Other applications, such as medical applications, especially skin bonding, prefer somewhat longer cure times, of a minute to two or three minutes to allow proper working and application before the material is set. Similarly, there are industrial and commercial applications where a longer time is desired to provide the user working time to apply and adjust the items being bonded without concern that the cure will set before the adjustment is made.

In addition to the effect on cure speed, it has been found that the alumina treatment may, and in most instances, if not all, also results in higher purity products. Specifically, in those experiments where GC and HPLC analyses of the monomer was performed before and after treatment with the alumina, it was found that certain impurities were either removed in total or, if they remained, they were present at reduced, oftentimes markedly lower, levels.

EXAMPLES

Having described the invention in general terms, Applicants now turn to the following non-limiting examples by which Applicants have demonstrated the utility and surprising benefit of the claimed process. Specifically, these examples demonstrate various processes in which a variety of alumina are used to treat various 1,1-disubstituted ethylene monomers under varying conditions. Further, these examples demonstrate the surprising attributes of the claimed processes, particularly with respect to the improved cure speed and consistent cure speed, enabling consistent and predictable results. Again, these examples are merely illustrative of the invention and are not intended to be or to be deemed limiting thereof. Those skilled in the art, having the benefit of this disclosure and the examples, will readily recognize many variations that may be applied and used in practicing the claimed invention and which are and are intended to be within the spirit of the invention and scope of the claims.

DMDEE Test

In order to assess cure performance of the 1,1-disubstituted ethylene monomers, a standardized test based on dimorpholinodiethyl ether ("DMDEE") as a cure initiator/activator was developed. This standardized test allowed direct comparison from treated and untreated 1,1-disubstituted ethylene monomers as well as between different types of treatments and variations of the same types of treatments. Specifically, the cure characteristics of 1,1-disubstituted ethylene monomers were assessed by inducing the polymerization of the monomers in the presence of DMDEE as follows:

DMDEE

To a tared 4 mL glass vial equipped with a magnetic stir bar, 55 microliters of a 10% by weight solution of DMDEE in isopropanol is added. The vial is reweighed to determine the weight of solution added and monomer is added to the DMDEE solution while stirring to give 1 mL monomer per 42.5 mg DMDEE solution. Stirring is continued for one minute. The stir bar is removed and replaced with a thermocouple. Temperature is plotted versus time. The polymerization induction time is taken as the time in which the rise in temperature between two successive data points (three point running average) first exceeds 0.5° C. A short induction time is indicative of a monomer that is suitably active for commercial use, i.e., will polymerize in a reasonable period of time. A long induction time is indicative of a monomer that, most likely due to the presence of impurities which inhibit polymerization, that is unsuitable for commercial use owing to the lack of polymerization or a cure speed that is too slow to be of commercial utility.

pH Determination pH of the alumina was determined by suspending 0.3 g of the alumina in 12 g neutral, deionized water (pH 6.7).

2.1.2 Monomers

Several batches of the 2.1.2 methylidene malonate monomer (Propanedioic acid, 2-methylene-, 1-(2-ethoxy-2-oxoethyl) 3-ethyl ester, Monomer A)

Monomer A were prepared using the Diels-Alder adduct process of U.S. Pat. Pub. No. 2010/0286438 A1 and the Iminium process of co-filed, co-pending US patent application of Gondi et. al., entitled "Improved Methylidene Malonate Process" and US Provisional Patent Application No. 61/591,884: the contents of all of which are hereby incorporated herein by reference. Again, although the products of these processes are characterized as monomer, it is to be appreciated that dimer, trimer, oligomer and/or low molecular weight polymer species were also present in the monomer compositions resulting therefrom.

In the case of those monomer compositions prepared according to the Diels-Alder process, the reaction mix generally comprised 4200 g of the anthracene adduct, 910 g maleic anhydride, 4.9 g hydroquinone and 4.9 g sulfuric acid. Following stripping of the methylidene malonate from the adduct, the reaction product was doubly distilled under vacuum to provide the 1,1-disubstituted ethylene monomer, Monomer A. For convenience, in those of the following examples using the adduct process generated monomer, each batch of Monomer A will be identified by the notation A-x(#) where x represents the batch number and (#), if present, represents the total number of distillations performed on that monomer. If no number is presented, it is the original double distilled material. If a (3) appears, then that indicates that the doubly distilled material was distilled a third time prior to use. Unless otherwise indicated, each monomer sample subjected to the alumina treatment was stabilized with 30 ppm trifluoroacetic acid (TFA) and 1000 ppm hydroquinone (HQ) prior to the alumina treatment and subsequently up-stabilized with and 30 ppm maleic acid (MA) and additional TFA to achieve a 30 ppm level following alumina treatment. It is thought that TFA and other anionic polymerization inhibitors are or may be lost to the alumina during treatment process. However, the alumina treatment appeared to have no effect on the level of free radical polymerization inhibitor, especially HQ; though additional quantities could be added following treatment if needed.

Comparative Examples 1-4

Example 1

Samples of Monomer A-1 were treated with several solid additives to assess their efficacy, if any, in enhancing the cure speed of the monomer. Each solid additive was added to the liquid monomer at a weight ratio of 15 mg solid/g monomer with continuous mixing for the five minutes contact time to essentially maintain an even dispersion of the solid particles in the liquid monomer. Following the five minute contact time, all samples including part of the control were filtered and then tested immediately in the DMDEE test. The results are shown in Table 1.

TABLE 1

| Example | Treatment | Induction Time (minutes) |
|---------|-----------|--------------------------|
| C1 | None - not filtered | 19.0 |
| C2 | None filtered | 17.3 |
| C3 | Potassium carbonate | No activity observed |
| C4 | Sodium bicarbonate | 17.8 |
| E1 | Neutral Alumina (pH 6.46) (Sigma Aldrich WN-3) | 14.8 |

As shown in Table 1, neither the potassium carbonate nor the sodium bicarbonate provided any improvement in cure speed. However, a significant and promising improvement was noted with the neutral alumina (14.8 minutes versus 17.3 minutes for the control). Additionally, the potassium carbonate and sodium bicarbonate samples polymerized after a couple days at room temperature, whereas the alumina treated monomer remained in liquid form.

Example 2

Neutral Alumina (WN-3) was used to treat two different monomers A-1 and A-2, both of which had low activity. The level of treatment was 6.5 weight percent (65 mg/g) alumina. Following alumina treatment portions of each of the samples, as well as untreated samples, were sealed in an ampoule. DMDEE testing was conducted immediately following sealing and again after 4 days storage at room temperature. Untreated Monomer A-1 had an induction time of ~19 minutes whereas untreated Monomer A-2 had an induction time of ~48 minutes. Treatment with alumina reduced the induction time to ~4.5 minutes in all cases. These results indicate that the improved cure speed is retained, even following sealing in ampoule.

Examples 3-7

A series of tests were conducted using three different batches of monomer, Monomer A-1, A-1(3) and A-2 and the neutral alumina from Example 1 but varying the amount of alumina, the temperature, and the contact time. The experimental details and results are shown in Table 2

TABLE 2

| Example | Monomer | Neutral Alumina (mg/g monomer) | Contact time/ Temperature | Induction Time (minutes) |
|---------|---------|--------------------------------|---------------------------|--------------------------|
| C1 | A-1 | None | N/A | 19.0 |
| E3 | A-1 | 30 | 5 min./25° C. | 16.1 |
| E4 | A-1 | 120 | 5 min./25° C. | 13.6 |
| E5 | A-1 | 120 | 120 min./50° C. | 2.7 |
| C2 | A-1(3) | None | N/A | >30 |
| E6 | A-1(3) | 120 | 120 min/50° C. | 2.2 |
| C3 | A-2 | None | N/A | >30 |
| E7 | A-2 | 120 | 120 min/50° C. | 3.1 |

The results shown in Table 2 for the controls are indicative that the problem with cure speed is a general one and not a batch specific issue. Furthermore, and more importantly, these results show that alumina treatment provides a consistent, repeatable improvement in cure speed, even from batch to batch, as compared to the controls. This improvement was especially remarkable for examples E5-E7 where a longer exposure time and higher temperature have a marked and pronounced effect on cure speed, as evident from the short induction times. Additionally, the results indicate that traditional efforts at improving cure speed, such as further distillation, did not have any effect; whereas, the combination of a third distillation and an alumina treatment provided even further improvement in cure speed. Indeed, the results suggest that some cure-inhibiting impurities may be removed in the distillation step(s) while others are removed in the alumina treatment. Clearly, alumina treatment, with or without additional distillations, is the key to achieving the desired improvement in cure characteristics, especially a short cure time.

Comparative Example 4

The doubly distilled Monomer A-2 was treated with colloidal silica, Aerosil 200 silica, at two weight loadings, 12 mg/g monomer and 26 mg/g monomer, and activated charcoal, DARCO 60, at 30 mg/g, for 2 hours at 50° C. Thereafter, the mixtures were filtered and the treated monomers subjected to the DMDEE test. No polymerization activity was observed within 30 minutes in either the non-treated control or in any of the treated samples. This demonstrates that other adsorbents are not effective in providing the enhanced cure performance, especially decreased induction time, as found with the alumina treatment.

Examples 8

Two timed series of alumina treatments on doubly distilled Monomer A-2 were conducted to assess the impact of contact time on the efficacy of the treatment process. In this case, neutral alumina (WN-3) was employed at two concentrations (6% and 8%) and at two different temperatures, 50° C. and 130° C. DMDEE testing was conducted on each sample treated at 50° C. at thirty minute intervals and at 120 minutes for that sample treated at 130° C. The test details and results are presented in Table 3.

TABLE 3

| Sample | Alumina (wt %) | Temperature (° C.) | Cure Time (minutes, DMDEE Test) | | | |
|--------|----------------|--------------------|-------|-----|-----|-----|
| | | | 30 | 60 | 90 | 120 |
| A | 6 | 50 | 7.8 | 4.9 | 4.3 | 4.3 |
| B | 6 | 130 | — | — | — | 5.1 |
| C | 8 | 50 | 5.4 | 3.5 | 3.2 | 2.6 |
| D | 8 | 130 | — | — | — | 3.4 |

These results indicate that the amount of alumina has more of an impact than the temperature at which the alumina treatment is conducted, although it is to be appreciated that temperature also plays a key role in performance of the alumina treatment. The results also indicate that the time of exposure also impacts cure speed, but that the effect tends to level as the duration of the treatment increases.

Example 9

A series of alumina treatments were performed using different alumina on two different monomers (A-1 and A-2) to assess the impact of the pH and form of the alumina on cure speed or induction time. The details of the testing and the results attained thereby are shown in Table 4. In each case the monomer was treated with the alumina for 2 hours at room temperature. For certain of the examples, as noted in Table 4, the alumina treatment was continued, at room temperature, for a total treatment time of 20.3 hours. Following the timed treatment, a portion of each sample was filtered and then subjected to the DMDEE test.

The results presented in Table 4 indicate that three key variables affect or have a direct impact upon the improvement in induction time: the alumina selected, the amount of alumina employed per volume of monomer to be treated, and the duration of the treatment. (As noted elsewhere, temperature is another key affecting alumina treatment efficacy.) In general, it is evident that more exposure of the monomer to the alumina, whether in terms of duration of weight ratio/amount, leads to a faster cure performance. It is recognized, however, that there is a limit in both respects. As noted, it was found that the effect levels off over time and one can increase cure speed only so much (from both a practical and actual perspective), regardless of the quantity of alumina. The results also demonstrate that a slightly acidic to moderately basic the alumina is necessary. Too acidic and the acidity will slow down cure as evident from the more acidic alumina BI* 7M9. Too basic and alumina and the monomer has a tendency to polymerize or, as shown by the Purum and Puriss aluminas (both pH 9.4+), no effect is seen.

TABLE 4

| Alumina | | | | Induction Time (Min.) | |
|---------|-----|---------------|------------------------|--------|-----------|
| Grade | pH□ | Amount (wt %) | Surface Area (m²/g)    | 2 hour | 20.3 hours |
| MONOMER A-1 | | | | | |
| None  | N/A | 0 | N/A | 19.3 | — |
| WN-3  | 6.5 | 6 | 155 | 5.8  | 0.7 |
| CG 20 | 7.2 | 4 | 125 | 3.7  | 0.8 |
| CG 20 | 7.2 | 6 | 125 | 1.7  | P |
| BI 409 | 6.9 | 6 | 150 | 2.9 | 0.6 |
| BI 409 | 6.9 | 8 | 150 | 1.8 | V |
| BI 7M9 | 5.4 | 6 | 150 | 15.5 | 10.6 |
| BI 7M9 | 5.4 | 8 | 150 | 16.6 | 12.9 |

TABLE 4-continued

| Alumina | | | | Induction Time (Min.) | |
|---|---|---|---|---|---|
| Grade | pH□ | Amount (wt %) | Surface Area (m²/g) | 2 hour | 20.3 hours |
| MONOMER A-2 | | | | | |
| None | N/A | 0 | N/A | | 48 |
| WN-3 | 6.5 | 6 | 155 | | 10 |
| WN-6 | ~7.5 | 6 | 200 | | 28 |
| CG-20 | 7.2 | 6 | 125 | | 9.8 |
| FP | 9.4+* | 6 | | | 44 |
| SP | 9.4+* | 6 | | | 49 |

□pH rounded to nearest 10$^{th}$.
*per manufactuer MSDS
All alumina materials were sourced from Sigma Aldrich. The following abbreviations are employed in this table: BI—Brockman I grade, FP—Fluka Purum, SP Sigma Puris, P—polymerized prior to DMDEE testing, V—slightly viscous.

Example 10

In order to assess the impact of moisture content of the alumina on the treatment of monomer, a sample of alumina (WN-3) was heated for 2 hours at 120° C. to drive off moisture. Thereafter, the alumina was cooled and then added at a 6 wt % level to Monomer A-4 and treated at 50° C. for 2 hours. No difference was seen on the induction time as between the dried and non-dried alumina. It is believed that a small difference in moisture plays little if any role in the efficacy of the treatment process; however, it has been found that water content can be transferred from the alumina to the monomer during the treatment process, which can adversely affect the monomer. Hence, it is generally preferable to use dry or low moisture content alumina.

Example 11

To assess whether the alumina treatment is more effective before or after the final distillation, two additional tests were conducted. Both employed 120 mg alumina (WN-3) per g of monomer.

In the first test, the treatment was conducted at 50° C. for 2 hours following which a portion of the monomer was subjected to DMDEE testing and showed an induction time of 4.1 minutes. The remaining monomer was then distilled using a thin film evaporative distillation. The DMDEE test was performed on the distillate. No polymerization was observed within 60 minutes.

In the second test, the alumina was added to the monomer and the mixture subjected to distillation to recover the monomer, leaving the alumina behind in the pot residue. The distillate was recovered and subjected to the DMDEE test and manifested an induction time of 28 minutes.

Although further testing is needed, it would appear, initially anyway, that alumina treatment should be conducted subsequent to any high temperature distillation processes.

Example 12

Monomer A-5 was treated with neutral alumina (WN-3) (0.12 g/g) for 2 hours at 50° C. and filtered. A portion of the filtrate was up-stabilized with 30 ppm trifluoroacetic acid (TFA). Both samples were subjected to the DMDEE test. The filtered monomer manifested an induction time of 0.8 minutes and the up-stabilized monomer an induction time of 3.5 minutes.

These results indicate that where the alumina treated monomer is highly activated, i.e., manifests a very short induction time, the 1,1-disubstituted ethylene can be stabilized for improved shelf stability while maintaining the good cure performance. This is especially important in commercial applications where there is a need to balance shelf stability with rapid cure rate.

Example 13

To show the ability to custom tailor cure speed, a composite batch of 2.1.2 monomer was prepared from several prior batches of monomer, each having been stabilized with 30 ppm TFA, 30 ppm Maleic acid, and 1000 ppm HQ. The monomer was treated with neutral alumina (WN-3) for 60 minutes and a portion was then up stabilized to 30 ppm TFA and 30 ppm maleic acid (alumina treatment is not seen to affect the level of HQ) following which the monomer was filtered and then sealed in glass ampoules. Monomer was removed from the ampoule and the cure speed tested and found to have been reduced from 44.6 minutes, prior to alumina treatment, to 7.2 minutes. The monomer was then subjected to an additional 30 minutes treatment with 0.5% neutral alumina which was found to further reduce the induction time to 5.0 minutes.

The remaining portion of the alumina treated composite batch was filtered and cure speed tested and the cure speed was found to have been reduced to ~2.7 minutes. The monomer was then up-stabilized, again to 30 ppm TFA and 30 ppm maleic acid, and cure speed tested. As a result of the added stabilizer, the cure speed had been reduced, with an induction time of ~5 minutes. The monomer was then sealed in glass ampoules and subsequently tested for cure speed. No change in the induction time of ~5 minutes was seen.

Example 14

To validate that the effect of the alumina treatment is not specific to methylidene malonates manufactured by the Diels-Adler adduct process, 2,1,2 methylidene malonate monomer was prepared according to the Iminium process of Gondi et. al., noted above. A portion of the isolated monomer was treated with neutral alumina and induction times tested for the treated and untreated monomer. It was found that the treatment resulted in the induction time dropping from 37 minutes to less than five minutes.

Example 15

Figure 1:
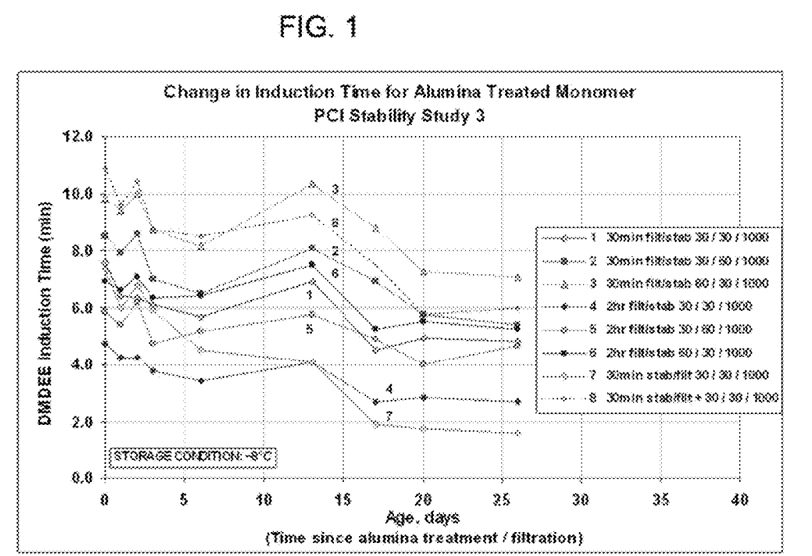
FIG. 1 is a graph showing the change in induction time of bulk 2.1.2 monomer under various conditions resulting from the study of Example 15.
Figure 2:
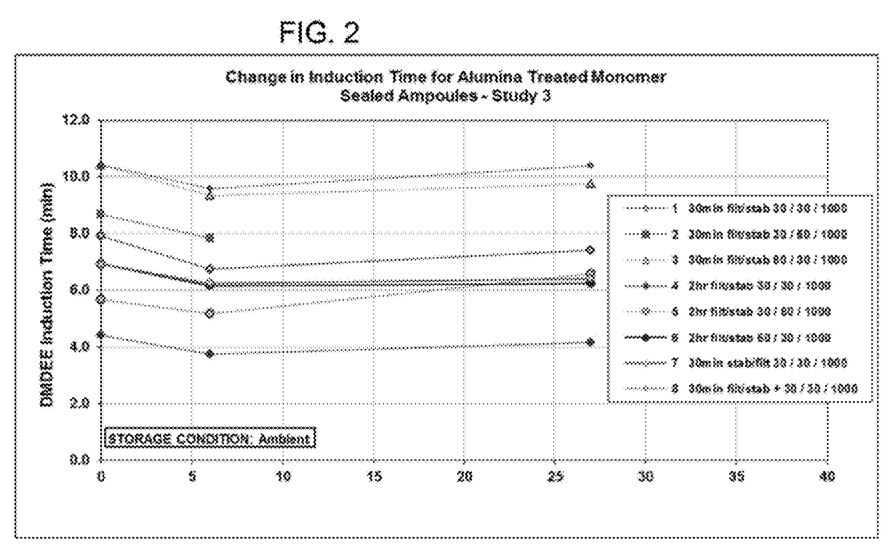
FIG. 2 is a graph showing the change in induction time of 2.1.2 monomer which has been sealed in glass ampoules according to the study of Example 15.

A further study was undertaken, again using 2.1.2 monomer, to assess the impact of a change in the duration of the treatment, the sequencing of the treatment and stabilization, and adjusting the amount of stabilizer used. The results and the specific conditions for each test were as shown in FIGS. 1 and 2. Specifically, FIG. 1 shows the results for bulk monomer stored in polyethylene bottles which had been treated with 6 wt % neutral alumina (WN-3) for either 30 or 120 minutes, and either filtered and then stabilized or stabilized and then filtered. The stabilizer packages were as presented in the figures with the numbers representing trifluoroacetic acid/maleic acid/hydroquinone (TFA/MA/HQ). FIG. 2 shows the results for the same monomer compositions with the exception that following filtration or, as appropriate, stabilization, the monomer was promptly sealed in glass.

As evident from the result shown in FIGS. 1 and 2, cure speed or induction time can be adjusted by altering the amount of stabilizers used, with, apparently, the TFA having a greater impact than MA in stabilizing the monomer composition and, hence, increasing the induction time. These results also reaffirm the finding that longer treatments provide better cure improvement. Finally, while FIG. 1 indicates that cure speed increases over time, the results in FIG. 2 show that cure speed remains fairly steady over time. It is believed that the increase in cure speed in FIG. 1 results from of a loss of anionic polymerization inhibitor, especially TFA, from the bulk monomer over time: a loss that is not possible in the case of the sealed monomer. This would lead one to employ sealed containers, particularly those impermeable to anionic, especially vapor phase anionic, stabilizers and/or avoid containers with large head space in commercial distribution of the monomer and products containing the same.

Example 16

2-octyl-α-cyanoacrylate monomer (Monomer B-1) is prepared following the general procedure outlined in Example 1 of U.S. Pat. No. 6,245,933. The preparation involves the reaction of ethyl cyanoacetate with paraformaldehyde in a Knoevenagel condensation, followed by transesterification using 2-octanol. The resultant polymer is cracked and distilled to give Monomer B-1.

A second cyanoacrylate monomer, ethyl α-cyanoacrylate (Monomer B-2) is prepared following the general procedure outlined in U.S. Pat. No. 7,569,719. The preparation involves the reaction of ethyl cyanoacetate with the iminium salt prepared from formaldehyde and t-butylamine under acidic conditions. After the reaction, sulfuric acid and hydroquinone is added to stabilize the reaction mixture and the mixture is distilled under reduced pressure to give Monomer B-2.

Portions of both Monomer B-1 and B-2 are subjected to the alumina treatment at 120 mg/g, 50° C. for 2 hours and the treated and untreated samples subjected to the DMDEE test.

Example 17

Following the general procedure outlined in Example 13 of WO 2010129066, diethyl methylidene malonate, Monomer C-1, is prepared. The preparation involves the reaction of diethyl malonate with paraformaldehyde in the presence of acetic acid. After the reaction, maleic acid and hydroquinone is added to stabilize the reaction mixture and the mixture is distilled under reduced pressure. Sulfuric acid and hydroquinone is added to stabilize the distillate and a second distillation is performed. The second distillate is stabilized with 15 ppm trifluoroacetic acid and 1000 ppm hydroquinone to give the diethyl methylidene malonate. A portion of the diethyl methylidene malonate is treated with neutral alumina (120 mg/g) at 50° C. for 2 hours. Both treated and untreated samples are subjected to the DMDEE test to demonstrate the enhanced cure performance of the treated versus the untreated materials.

Although the present invention has been described with respect to aforementioned specific embodiments and examples, it should be appreciated that other embodiments utilizing the concept of the present invention are possible without departing from the scope of the invention. The present invention is defined by the claimed elements and any and all modifications, variations, or equivalents that fall within the spirit and scope of the underlying principles embraced or embodied thereby.

We claim:

1. A process for improving the cure characteristics of a 1,1-disubstituted ethylene having one or two electron withdrawing substituents at the 1 position which process comprises contacting the 1,1-disubstituted ethylene with alumina having a pH that ranges from slightly acidic to moderately basic so as to reduce the induction time for cure of said 1,1-disubstituted ethylene as compared to the same material which has not been so treated, wherein the induction time for cure is reduced by conducting the alumina treatment at from about 0° C. to about 150° C. and for from about 5 minutes to about 20 hours.

2. The process of claim 1 wherein the 1,1-disubstituted ethylene is an ethylene monomer, dimer, timer, oligomer or low molecular weight polymer or a combination of any one or two of the foregoing.

3. The process of claim 1 wherein the 1,1-disubstituted ethylene comprises a monomer or monomer composition.

4. The process of claim 1 wherein at least one of the electron withdrawing substituents is selected from the group consisting of cyano, carboxylic acid, carboxylic esters, amides, ketones and formyl.

5. The improved process of claim 1 wherein the 1,1-disubstituted ethylene has the general formula:

wherein R is selected from the group consisting of H and $C_1$ to $C_6$ hydrocarbyl, X is selected from the group consisting of $C_1$ to $C_6$ hydrocarbyl, cyano, carboxylic acid, carboxylic acid esters, amides, ketones and formyl and Y is selected from the group consisting of cyano, carboxylic acid, carboxylic acid esters, ketones and formyl.

6. The improved process of claim 5 wherein R is H and X and Y are independently selected from the group consisting of cyano and carboxylic acid esters.

7. The process of claim 5 wherein the 1,1-disubstituted ethylene has the general formula:

wherein X is selected from the selected from the group consisting of cyano and carboxylic acid esters and $R_1$ is a $C_1$ to $C_6$ hydrocarbyl group.

8. The process of claim 7 wherein the 1,1-disubstituted ethylene is selected from the group consisting of 9. The process of claim 1 further comprising the step of isolating the treated 1,1-disubstituted ethylene from the alumina.

10. The process of claim 1 wherein the alumina has a pH of from 5.0 to 8.5.

11. The process of claim 1 wherein the alumina has a pH of from 5.5 to 8.0.

12. The process of claim 1 wherein the 1,1-disubstituted ethylene is contacted with alumina at a temperature of from 10° C. to 70° C.

13. The process of claim 1 wherein 1,1-disubstituted ethylene is contacted with alumina at a temperature of from 25° C. to 60° C.

14. The process of claim 1 wherein the treatment is conducted in a batch format by combining a set amount of the 1,1-disubstituted ethylene with from about 0.5 to about 20 weight percent of the alumina based on the weight of the 1,1-disubstituted ethylene.

15. The process of claim 1 wherein the treatment is conducted in a batch format combining a set amount of the 1,1-disubstituted ethylene with from about 1 to about 15 weight percent of the alumina based on the weight of the 1,1-disubstituted ethylene to form a slurry.

16. The process of claim 15 wherein the slurry is allowed to sit, with or without stirring, for from about 5 minutes up to 20 hours.

17. The process of claim 15 wherein the slurry is allowed to sit, with or without stirring, for from about 10 minutes up to 5 hours.

* * * * *